(12) United States Patent
Murillo

(10) Patent No.: US 7,137,950 B1
(45) Date of Patent: Nov. 21, 2006

(54) SYSTEM AND APPARATUS FOR INSPECTION OF FEET

(76) Inventor: Albert Murillo, 675 Redondo La., Templeton, CA (US) 93465

(*) Notice: Subject to any disclaimer, the term of this patent is extended or adjusted under 35 U.S.C. 154(b) by 0 days.

(21) Appl. No.: 11/136,352

(22) Filed: May 23, 2005

(51) Int. Cl.
   *A61B 1/247* (2006.01)

(52) U.S. Cl. .................................... 600/247

(58) Field of Classification Search ........ 600/247–248, 600/189; 359/850, 857, 872, 879; 362/133, 362/138–9; 132/73.5, 296, 301, 304, 316
See application file for complete search history.

(56) References Cited

U.S. PATENT DOCUMENTS

| | | | | |
|---|---|---|---|---|
| 1,643,626 A | * | 9/1927 | May | 359/857 |
| 1,692,943 A | * | 11/1928 | Lelyveld | 359/872 |
| 1,743,469 A | * | 1/1930 | May | 359/872 |
| 2,009,340 A | * | 7/1935 | Edwards | 600/592 |
| 2,112,399 A | * | 3/1938 | Graham | 359/854 |
| 2,136,832 A | * | 11/1938 | Weisberger | 600/248 |
| 2,382,131 A | * | 8/1945 | Cameron | 359/860 |
| 2,480,361 A | * | 8/1949 | Doumitt | 600/592 |
| D176,451 S | * | 12/1955 | Ennen | D6/310 |
| 4,534,365 A | * | 8/1985 | Bonetta et al. | 600/592 |
| 5,025,476 A | * | 6/1991 | Gould et al. | 382/115 |
| 5,959,791 A | * | 9/1999 | Bagnato, III | 359/872 |
| 6,352,347 B1 | * | 3/2002 | Unema | 359/850 |
| 6,598,992 B1 | * | 7/2003 | Ames | 362/138 |

* cited by examiner

*Primary Examiner*—Patricia Bianco
*Assistant Examiner*—Patrick J. Kilkenny
(74) *Attorney, Agent, or Firm*—Andrew Y. Schroeder; Law Offices of Andrew Y. Schroeder; Andrew Y. Schroeder

(57) ABSTRACT

An apparatus for inspecting feet comprising a left vertical wall, a right vertical wall, a top wall, a bottom wall, a left side mirror, a right side mirror, a center mirror, and a top mirror; said left vertical wall is attached to a first end of said bottom wall, said right vertical wall is attached to a second end of said bottom wall, said top wall is attached to top end of said left vertical wall and top end of said right vertical wall via hinging means, said top mirror is affixed to a bottom side of top wall via affixing means; said center mirror is affixed substantially in the center to bottom wall via affixing means; said right side mirror is affixed to bottom wall substantially adjacent to said center mirror via affixing means; said left side mirror is affixed to bottom wall substantially adjacent to said center mirror via affixing means.

20 Claims, 8 Drawing Sheets

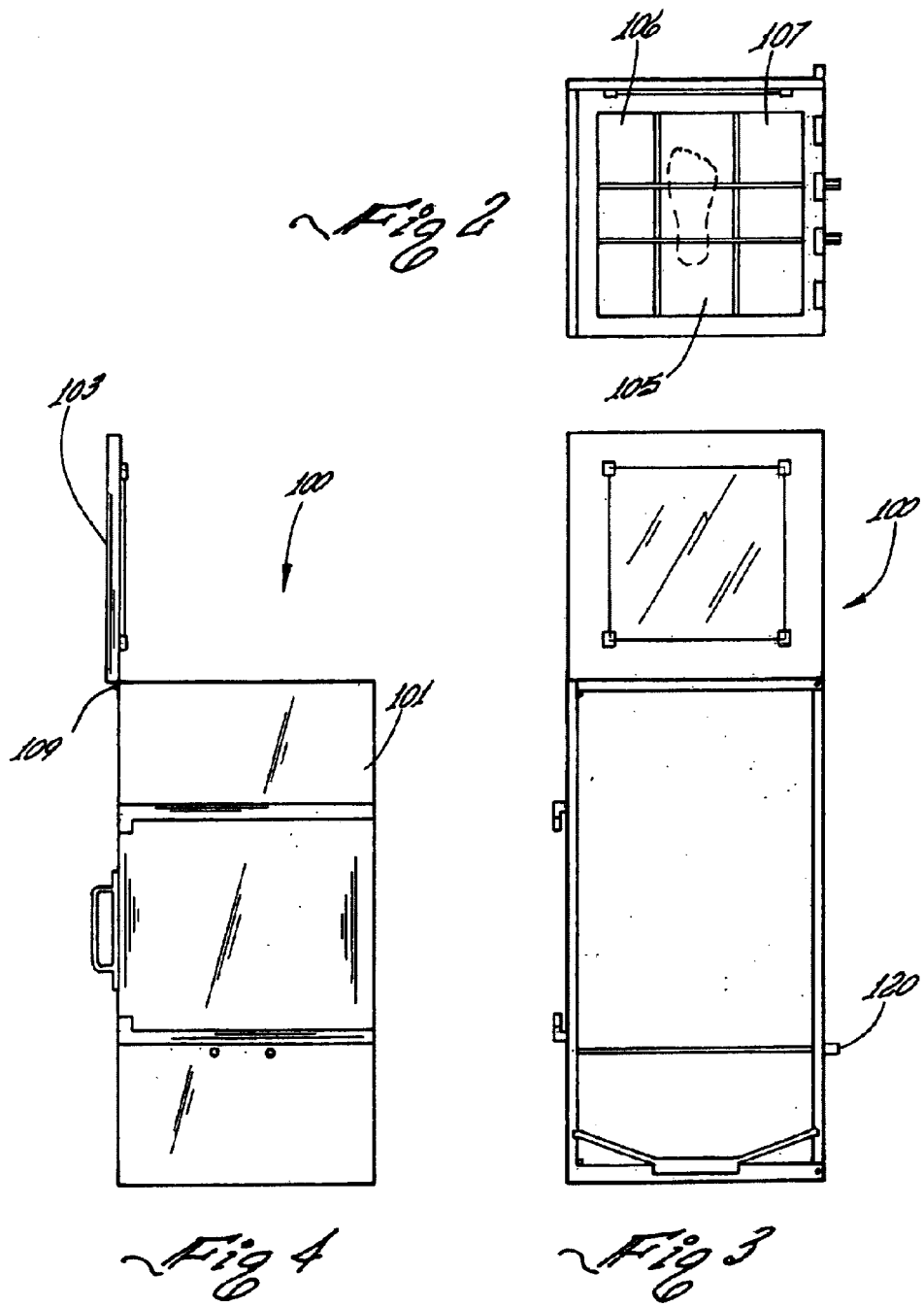

SYSTEM AND APPARATUS FOR INSPECTION OF FEET

FIELD OF THE INVENTION

The present invention is in the area of medical equipment, and more specifically relates to apparatus and methods for inspecting feet.

BACKGROUND OF THE INVENTION

Diabetes poses grave health dangers to people which include death, amputation, and gangrene. If people suffering with diabetes do not properly regulate their diet, check for gangrene and the other safety protocols associated therewith, serious consequences may ensue.

One particular problem Diabetes poses relates to the feet of the victims. Oftentimes, complications such as blisters, bruises, rashes, in-grown toenails, etc on a diabetes victim will manifest themselves on the soles of a victim's foot. If these problems are not properly treated in time, these complications will exacerbate to the point where the foot becomes infected with gangrene. Once gangrene sets in and accumulates in one's foot, a doctor may have no choice to amputate the gangrenous infected area in order to prevent its spread to the rest of the body.

Unfortunately, many Diabetes patients are elderly people who cannot properly examine the soles of their own feet (Diabetes can also affect the young and sometimes manifest with babies). These elderly people have less flexibility and are oftentimes overweight. Therefore, the only way to ensure proper inspection of their own feet is to either have a doctor do it for them or have another person inspect it. However, having other people inspect one's own feet may be awkward and a bit embarrassing.

Currently, the marketplace does not provide for a method or apparatus for the self-inspection of one's own feet. Therefore, what is clearly needed is an apparatus, system and methods thereof to properly inspect one's own feet daily.

SUMMARY OF THE INVENTION

An apparatus for inspecting feet comprising a left vertical wall, a right vertical wall, a top wall, a bottom wall, a left side mirror, a right side mirror, a center mirror, and a top mirror; said left vertical wall is attached to a first end of said bottom wall, said right vertical wall is attached to a second end of said bottom wall, said top wall is attached to top end of said left vertical wall and top end of said right vertical wall via hinging means, said top mirror is affixed to a bottom side of top wall via affixing means; said center mirror is affixed substantially in the center to bottom wall via affixing means; said right side mirror is affixed to bottom wall substantially adjacent to said center mirror via affixing means; said left side mirror is affixed to bottom wall substantially adjacent to said center mirror via affixing means.

In some preferred embodiments, the apparatus further comprises feet holding bars, said feet holding bars to pass longitudinally through holes located on said left vertical wall and said right vertical wall.

In other preferred embodiments, the apparatus has an upper end of left vertical member and an upper end of right vertical member are dovetailed shaped to engageably attach with said top wall, said top wall is dovetail shaped to engageably attach with said right vertical member and left vertical member. In other preferred embodiments, the apparatus has a center mirror which is magnified.

In some preferred embodiments, the apparatus may include a center mirror which is magnified. In other preferred embodiments, the apparatus has a center mirror which is placed in a groove located on said bottom wall. In other preferred embodiments, the apparatus has a left side mirror which is substantially tilted at an angle. In other preferred embodiments, the apparatus has a right side mirror which is substantially tilted at an angle.

In some preferred embodiments, the apparatus has an upper end of right vertical member and said upper end of left vertical member has a dovetail hole passing longitudinally through dovetail interfaces. In other preferred embodiments, the apparatus further comprises a locking bar which passes through said hole. In addition, the apparatus may be composed of wood, metal, or plastic.

In some preferred embodiments, the apparatus further comprises a light means affixed to either said right vertical member or said left vertical member. In other preferred embodiments, the apparatus further comprises a light means affixed to either said right vertical member or said left vertical member. And in other preferred embodiments, the apparatus has feet holding bars which are made of metal.

BRIEF DESCRIPTION OF THE DRAWING FIGURES

FIG. 2 is a is a plan view of an exemplary embodiment of the present invention.

FIG. 3 is a plan view of a preferred embodiment of the present invention.

FIG. 4 is a plan view of a preferred embodiment of the present invention.

Figure 9A:
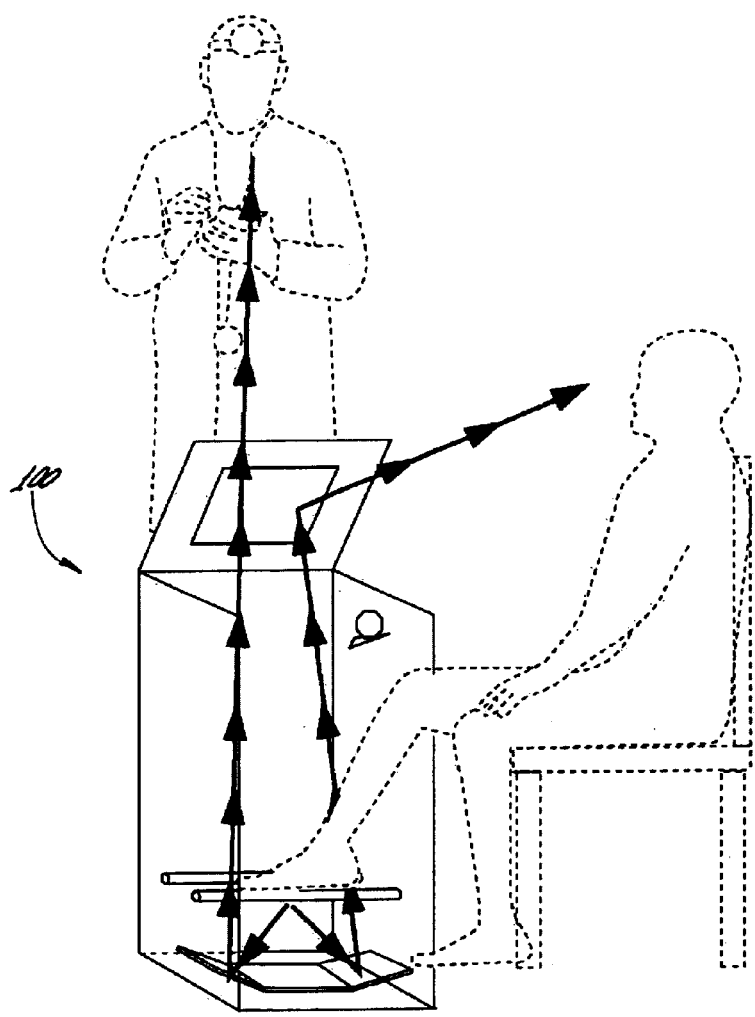

FIG. 9*a* is a perspective view of a preferred embodiment of the present invention.

FIG. 9*a* is a perspective view of a preferred embodiment of the present invention.

Figure 9B:
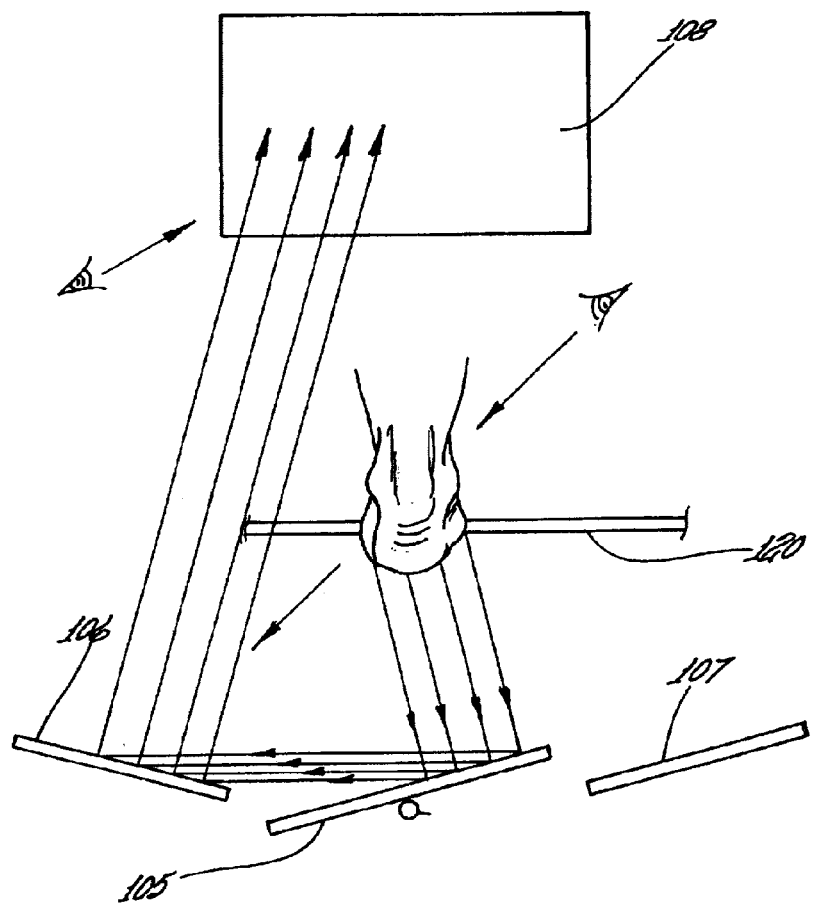

FIG. 9*b* is a perspective view of a preferred embodiment of the present invention.

Figure 9C:
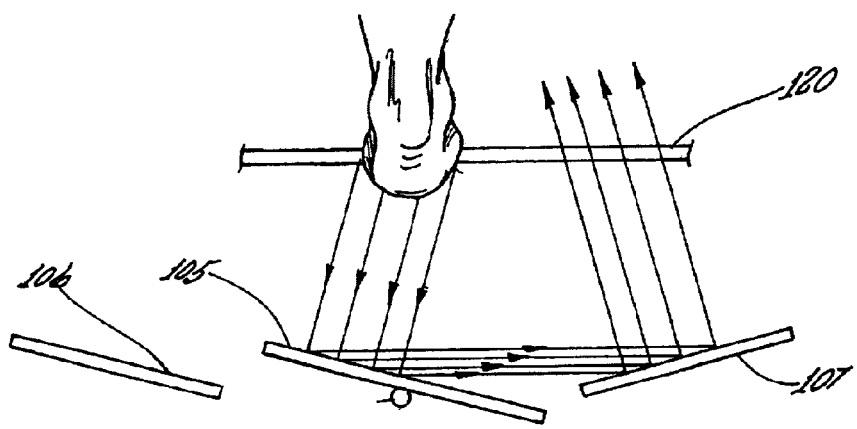

FIG. 9*c* is a perspective view of a preferred embodiment of the present invention.

Figure 9D:
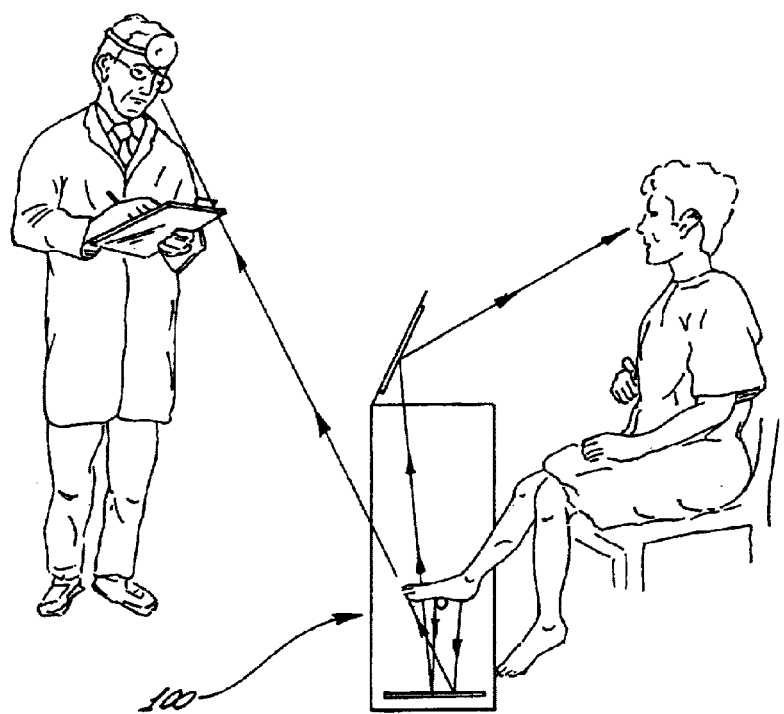

FIG. 9*d* is a perspective view of a preferred embodiment of the present invention.

DESCRIPTION OF PREFERRED EMBODIMENTS

According to a preferred embodiment of the present invention, a unique method, system, and apparatus is used to inspect the feet of a person. This foot inspection may be used by diabetes patients to search for blisters, bruises, rashes, in-gown toenails, red spots, etc. on the soles of their feet. Said method, apparatus, and system may also be used for other foot inspection purposes as well. Moreover, this system is designed to be used by caregivers such as medical doctors podiatrists, nurses, physician's assistants etc. for the purpose of evaluating and diagnosing any feet related maladies. In some preferred embodiments, the present invention is used by a caregiver to show the patient where there are any feet related maladies and use the present invention to explain to the patient how they can treat said maladies. The present invention is also designed to be used at home by people for the purpose of self-evaluation. The method, apparatus, and system are described in enabling detail below.

The present invention is designed such that a patient may evaluate a person's foot through the view given by the top mirror. Or, in the alternative, a patient and/or caregiver may use the assemblage of mirrors in such a way to examine all regions of the feet from top to bottom as well as the sides of the feet. The present invention will also enable both the patient and/or caregiver to examine the foot from the same angle and in the same light. The caregiver will be able to view the patient's foot through the rear of the apparatus as is illustrated in FIGS. 9a and 9d. It should be noted here that the side facing the caregiver in FIG. 9d is open, just as it is open on the patient's side.

Figure 1:
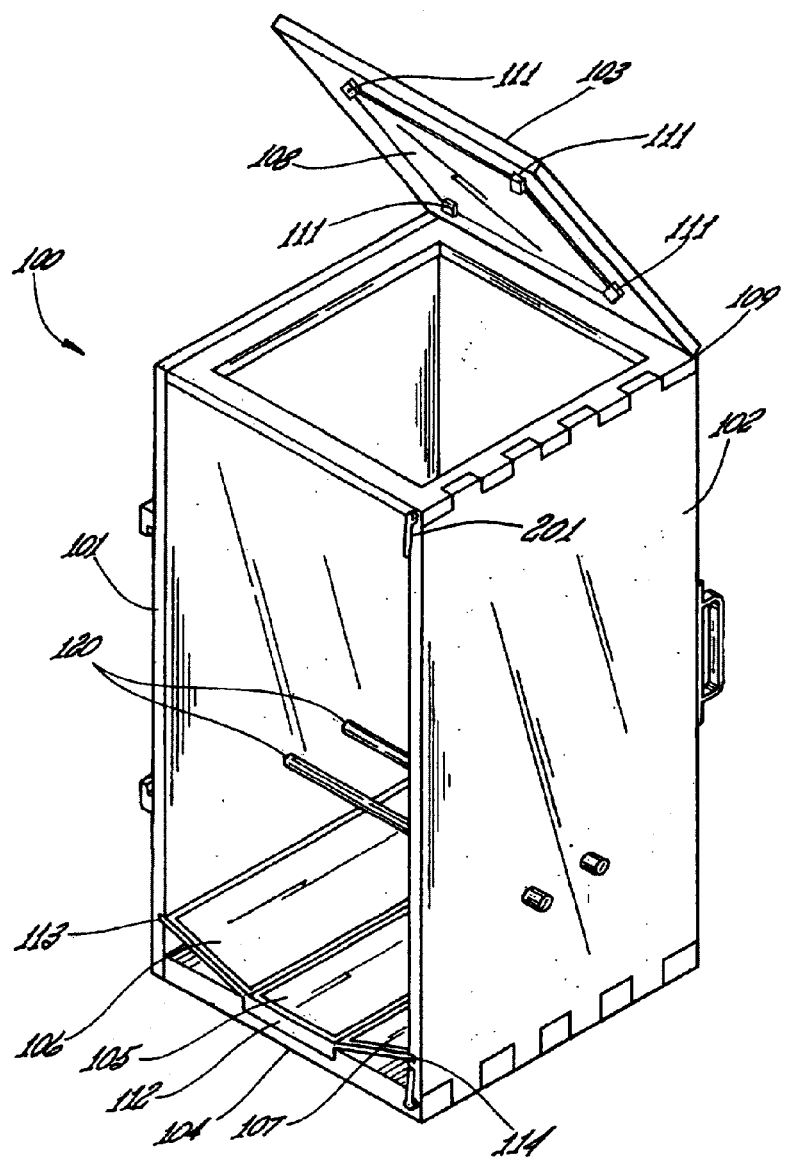
FIG. 1 is a perspective view of an exemplary system according to an embodiment of the present invention.
Figures 5, 6:
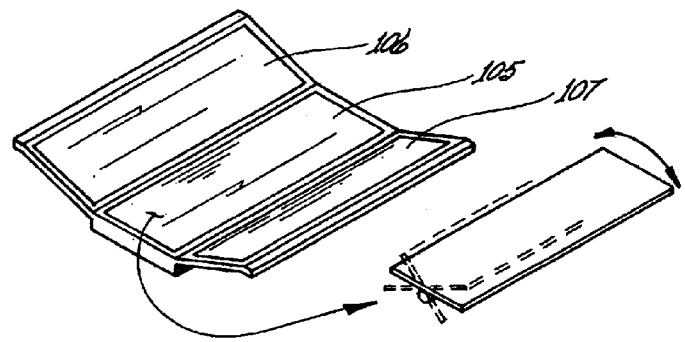
FIG. 5 is a perspective view of a preferred embodiment of the present invention.
FIG. 6 is a perspective view of a preferred embodiment of the present invention.

FIG. 1 shows a preferred embodiment of the present invention. Apparatus frame 100 comprises vertical wall 1 101, vertical wall 2 102, top wall 103, and bottom wall 104. FIG. 2 illustrates the mirrors of a preferred embodiment of the present invention. Attached to bottom wall is bottom mirror 105, side mirror 1 106, and side mirror 2 107. Top mirror 108 is affixed to top wall 103 by affixing means 111. FIGS. 5 and 6 is another view of said mirrors.

FIGS. 9a–d illustrate the views by which a person may view the soles of their feet. Essentially, a person will be able to view the soles and sides of their feet through the top mirror. The top mirror, in turn, receives its image through light directed from the bottom mirrors.

FIGS. 3 and 4 illustrate other angles of a preferred embodiment of the present invention. Top wall 103 is affixed to vertical wall 1 101 and vertical wall 2 102 via hinging means 109. Hinging means 109 enables top wall 103 along with attendant top mirror 108 to rotate about an axis. Hinging means 109 is preferably able to hold into place both top mirror 108 and top wall 103 in a stationary position along any angle which is most convenient for user. Or in the alternative, an elongated member may also be affixed to either vertical wall 1 101 or vertical wall 2 102 to hold into place top wall 103.

Apparatus frame 100 may be composed of a panoply of materials. Just about any type of material may be used in order to make the apparatus operationally functional. Exemplary materials include plastic, wood, polymer, steel, aluminum, cardboard, and even fabric. In a preferred embodiment, the composition of apparatus frame 100 is lightweight.

Bottom mirror 105 in a preferred embodiment is magnified for the purpose of proper inspection of feet. Bottom mirror 105 in some embodiments may have a regular mirror which is not magnified on the opposite side. Therefore, bottom mirror 105 in some embodiments is double-sided: a magnified mirror on one side and a regular mirror on the other side.

Side mirror 1 106 and side mirror 2 107 are angled in such a fashion such that they face each other. All three mirrors are affixed to Apparatus frame 100 via affixing means 111. Affixing means 111 are inconsequential to the present invention because there are a panoply of means to do so. A person skilled in the art would be able to quickly discern how to do so. Moreover, as with the bottom mirror 105, side mirror 1 106 and side mirror 2 107 are also inclinable about an axis. This adjustability enables viewing of the foot by either the patient individually, or by the caregiver. The adjustability also enables one to see different angles and all regions of a bottom of one's foot. In addition, it should be pointed out here that in some preferred embodiments, all of the lower mirrors may be independently adjustable and inclinable with respect to each other.

Affixed substantially in the lower portion of the Apparatus frame 100 are feet holders 120. In a preferred embodiment feet holders 120 are long elongated rods which are affixed to Apparatus frame 100 by simply placing feet holders 120 through their respective holes 121 in Apparatus frame 100 through one side and out the other.

The composition used for feet holders 120 is of no consequence. Any material which is strong enough to withhold the weight of a person's feet/leg upon the feet holders 120 is expedient for the task. In preferred embodiments feet holders 120 are made of steel, plastic, polymer, or even aluminum.

In other embodiments feet holders 120 may also be made of a flexible lightweight material such as nylon or cloth. There are many other embodiments which can be used to hold a person's feet. A person skilled in the art would know how to do so. As such, the particular way the feet are held above the mirrors is inconsequential.

Figure 7:
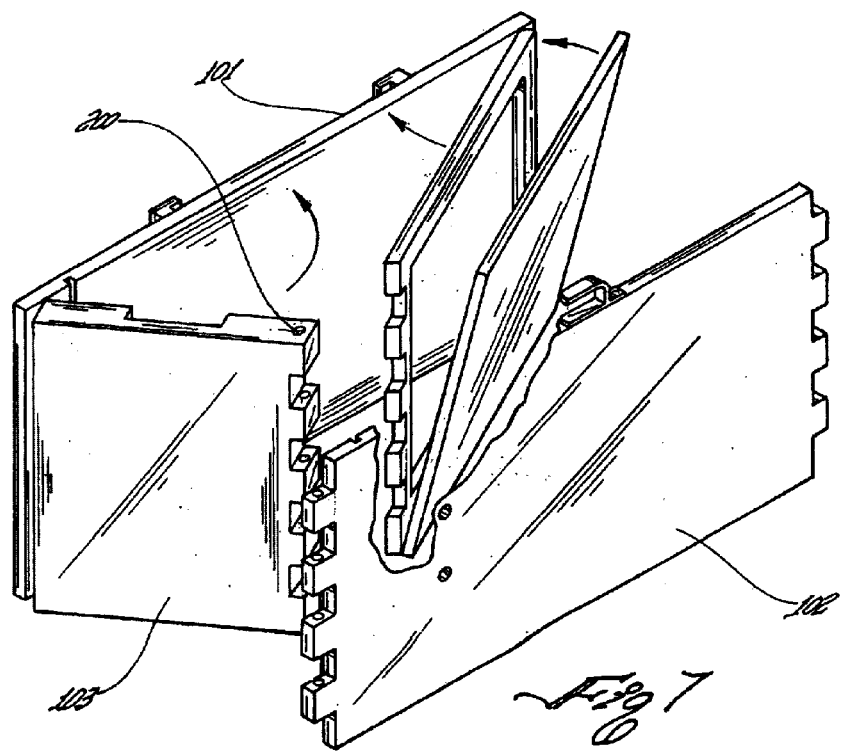
FIG. 7 is a perspective view of a preferred embodiment of the present invention.

FIG. 7 illustrates another preferred embodiment of the present invention which is made to be collapsible. Both vertical wall 1 and vertical wall 2 are made to have dovetail shapes to fit and conjoin with top wall 103. A hole 200 is located longitudinally through the dovetail edges to house locking member 201. Locking member 201 is made to fit into hole 200 in order to lock vertical walls with top wall 103.

Figure 8:
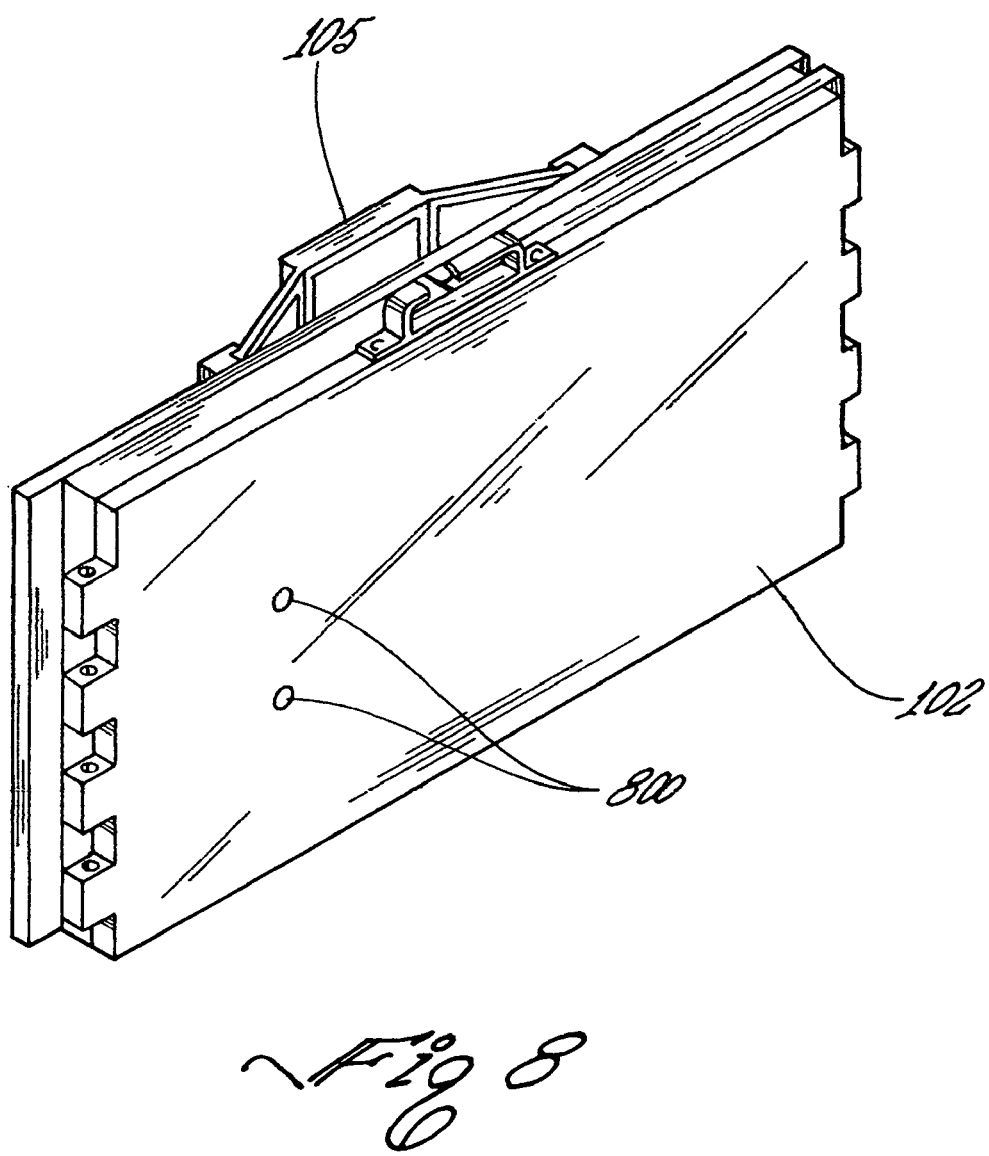
FIG. 8 is a perspective view of a preferred embodiment of the present invention.

FIGS. 7 and 8 illustrates a preferred embodiment of the present invention and shows how a preferred embodiment of the present invention may be collapsed in order to become portable. First, top wall 103 is disconnected from vertical wall by pulling out locking member 201 from the hole 200. Then, top wall 103 is placed against vertical wall and the other vertical wall is disconnected.

It will be apparent to the skilled artisan that there are numerous changes that may be made in embodiments described herein without departing from the spirit and scope of the invention. As such, the invention taught herein by specific examples is limited only by the scope of the claims that follow.

What is claimed is:

1. An apparatus for inspecting feet comprising a left vertical wall, a right vertical wall, a top wall, a bottom wall, a left side mirror, a right side mirror, a center mirror, and a top mirror;

said left vertical wall is attached to a first end of said bottom wall, said right vertical wall is attached to a second end of said bottom wall, said top wall is attached to top end of said left vertical wall and top end of said right vertical wall via means for hingeably connecting, said top mirror is affixed to a bottom side of top wall via means for affixing;

said center mirror is affixed substantially in the center to bottom wall via means for affixing;

said right side mirror is affixed to bottom wall substantially adjacent to said center mirror via means for affixing;

said left side mirror is affixed to bottom wall substantially adjacent to said center mirror via means for affixing.

2. The apparatus of claim 1 further comprising feet holding bars, said feet holding bars to pass longitudinally through holes located on said left vertical wall and said right vertical wall.

3. The apparatus of claim 1 wherein an upper end of left vertical member and an upper end of right vertical member are dovetailed shaped to engageably attach with said top wall, said top wall is dovetail shaped to engageably attach with said right vertical member and left vertical member.

4. The apparatus of claim 1 wherein said center mirror is magnified.

5. The apparatus of claim 3 wherein said center mirror is magnified.

6. The apparatus of claim 1 wherein said center mirror is placed in a groove located on said bottom wall.

7. The apparatus of claim 1 wherein said left side mirror is substantially tilted at an angle.

8. The apparatus of claim 1 wherein said right side mirror is substantially tilted at an angle.

9. The apparatus of claim 3 wherein said upper end of right vertical member and said upper end of left vertical member has a dovetail hole passing longitudinally through dovetail interfaces.

10. The apparatus of claim 8 further comprising a locking bar which passes through said hole.

11. The apparatus of claim 1 which is composed of plastic.

12. The apparatus of claim 1 which is composed of wood.

13. The apparatus of claim 1 which is composed of metal.

14. The apparatus of claim 3 which is composed of plastic.

15. The apparatus of claim 3 which is composed of wood.

16. The apparatus of claim 3 which is composed of metal.

17. The apparatus of claim 1 further comprising a light means affixed to either said right vertical member or said left vertical member.

18. The apparatus of claim 3 further comprising a light means affixed to either said right vertical member or said left vertical member.

19. The apparatus of claim 2 wherein said feet holding bars are made of plastic.

20. The apparatus of claim 2 wherein said feet holding bars are made of metal.

* * * * *